(12) United States Patent
Yuan

(10) Patent No.: US 7,289,310 B1
(45) Date of Patent: Oct. 30, 2007

(54) ADJUSTABLE STATIC CURRENT DISCHARGING BRACELET

(76) Inventor: Chun-An Yuan, P.O. Box 697, Fongyuan City 420, Taichung County (TW)

( * ) Notice: Subject to any disclaimer, the term of this patent is extended or adjusted under 35 U.S.C. 154(b) by 0 days.

(21) Appl. No.: 11/656,999

(22) Filed: Jan. 24, 2007

(51) Int. Cl.
*H01H 47/00* (2006.01)

(52) U.S. Cl. ............... 361/220; 361/212; 361/230; 361/231; 361/232; 361/233

(58) Field of Classification Search ........... 361/212, 361/220, 230–233; 57/901; 439/37; 24/68 J, 24/69 J, 71 J, 71 R
See application file for complete search history.

(56) References Cited

U.S. PATENT DOCUMENTS

| | | | | |
|---|---|---|---|---|
| 4,398,277 A | * | 8/1983 | Christiansen et al. | 361/220 |
| 4,577,256 A | * | 3/1986 | Breidegam | 361/220 |
| 4,662,695 A | * | 5/1987 | Gordon et al. | 439/92 |
| 4,720,765 A | * | 1/1988 | Weiss | 361/220 |
| 4,816,964 A | * | 3/1989 | Weiss | 361/220 |
| 5,036,423 A | * | 7/1991 | Williams | 361/212 |
| 5,184,274 A | * | 2/1993 | Weiss | 631/220 |
| 5,754,389 A | * | 5/1998 | Hsu | 361/220 |
| 6,215,639 B1 | * | 4/2001 | Hee | 361/212 |
| 6,401,307 B1 | * | 6/2002 | Wild | 24/71 J |
| 6,426,859 B1 | * | 7/2002 | Cohen | 361/220 |
| 6,944,916 B2 | * | 9/2005 | Kawagoe | 24/71 J |

* cited by examiner

*Primary Examiner*—Michael Sherry
*Assistant Examiner*—Terrence R. Willoughby

(57) ABSTRACT

An adjustable static current discharging bracelet includes a main body of inverse U-shaped section, a medium static current collector under the top of the main body and riveted to a protruding rod, a positioning device under the medium static current collector, a lower static current collector under the positioning device, a link having one end connected fixedly with the medium and lower static current collectors and the inlaid holes of the main body, and the other end connected to one end of the positioning device which has a pair of elastic retaining blocks engaged with a pair of serrated alignments of the main body. When press a pair of buttons inward to disengaged the elastic retaining blocks with a pair of serrated alignments of the main body, the positioning device together with one end of the link enable to slide on a pair of slender guides of the main body to adjust the length of the link.

1 Claim, 6 Drawing Sheets

(2-2)

(2'-2')

(2"-2")

(2'''-2''')

US 7,289,310 B1

ADJUSTABLE STATIC CURRENT DISCHARGING BRACELET

BACKGROUND OF THE INVENTION

The present invention relates to static current discharging bracelet and more particularly to an adjustable static current discharging bracelet which enables the user to conveniently adjust the tension and relaxation of the link of bracelet.

In order to avoid the defect products, the workers in the high tech electronic industries ought to wear a static current discharging bracelet on their wrists, in corporation with a grounding wire that the static current in their bodies is therefore discharged. Due the size of the wrists of everybody are not the same, the workers have to adjust the tension and relaxation of the link for their bracelets. The conventional way to adjust the link is to open the pinch plate of the bracelet. Then adjusts the length of the link and then closes the pinch plate to its original position. It is very inconvenient and wasting of time that the work must be flustered to finish the above steps with one hand.

SUMMARY OF THE PRESENT INVENTION

The present invention has a main object to provide an adjustable static current discharging bracelet which has a pair of elastic buttons sliding in concert with a positioning device which has one end connecting to one end of the link of bracelet. The user only uses a thumb and an index finger to operate the buttons, the length of the link is decided. It is very convenient and not affect their job performance.

Accordingly, the adjustable static current discharging bracelet of the present invention comprises:

a main body of inverse U-shaped section having a protruding rod on a central top partially extending to the inside, at least a guide on under side, a pair of serrated alignment on the inner side of the lateral walls, a sliding slot under each of the serrated alignments;

a medium static current collector positioned inside the main body beneath the protruding rod and connected with the protruding rod and having one end connecting to one end of the link;

a positioning device under the medium static current collector having a pair of elastic retaining blocks and a sliding plate, the sliding plate is sliding in concert with the elastic retaining block on the guide of the main body. The sliding plate has one end connected to the other end of the link;

a lower static current collector under the sliding plate and connected to the main body. Therefore presses the elastic buttons inward to have the retaining blocks disengaged with the serrated alignment and free to slide in concerted with the sliding plate, the length of the link is adjusted.

The present invention will become more fully understood by reference to the following detailed description thereof when read in conjunction with the attached drawings.

DETAILED DESCRIPTION OF THE PREFERRED EMBODIMENT

Figure 1:
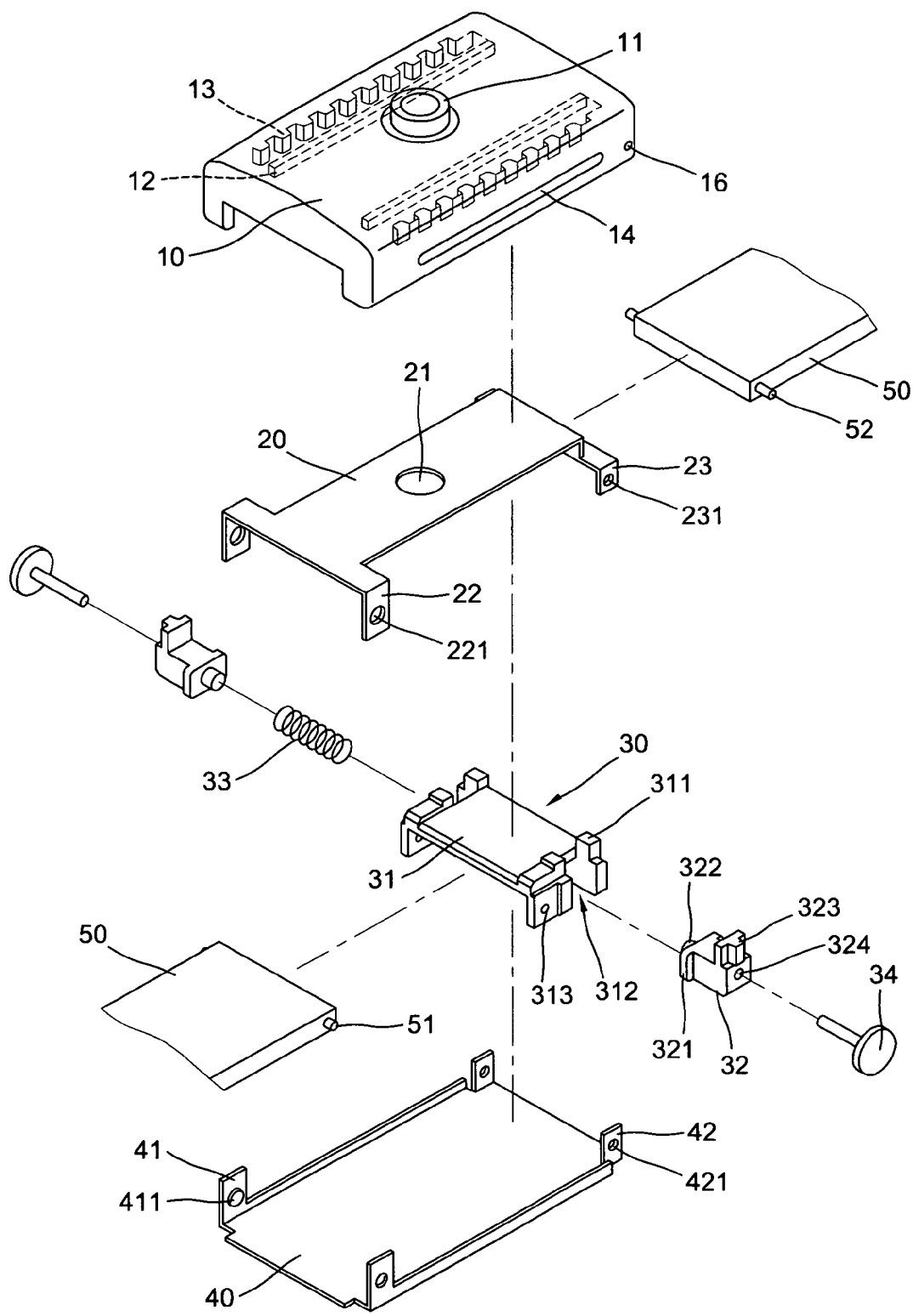
FIG. 1 is an exploded perspective of the preferred embodiment of the present invention.
Figure 2:
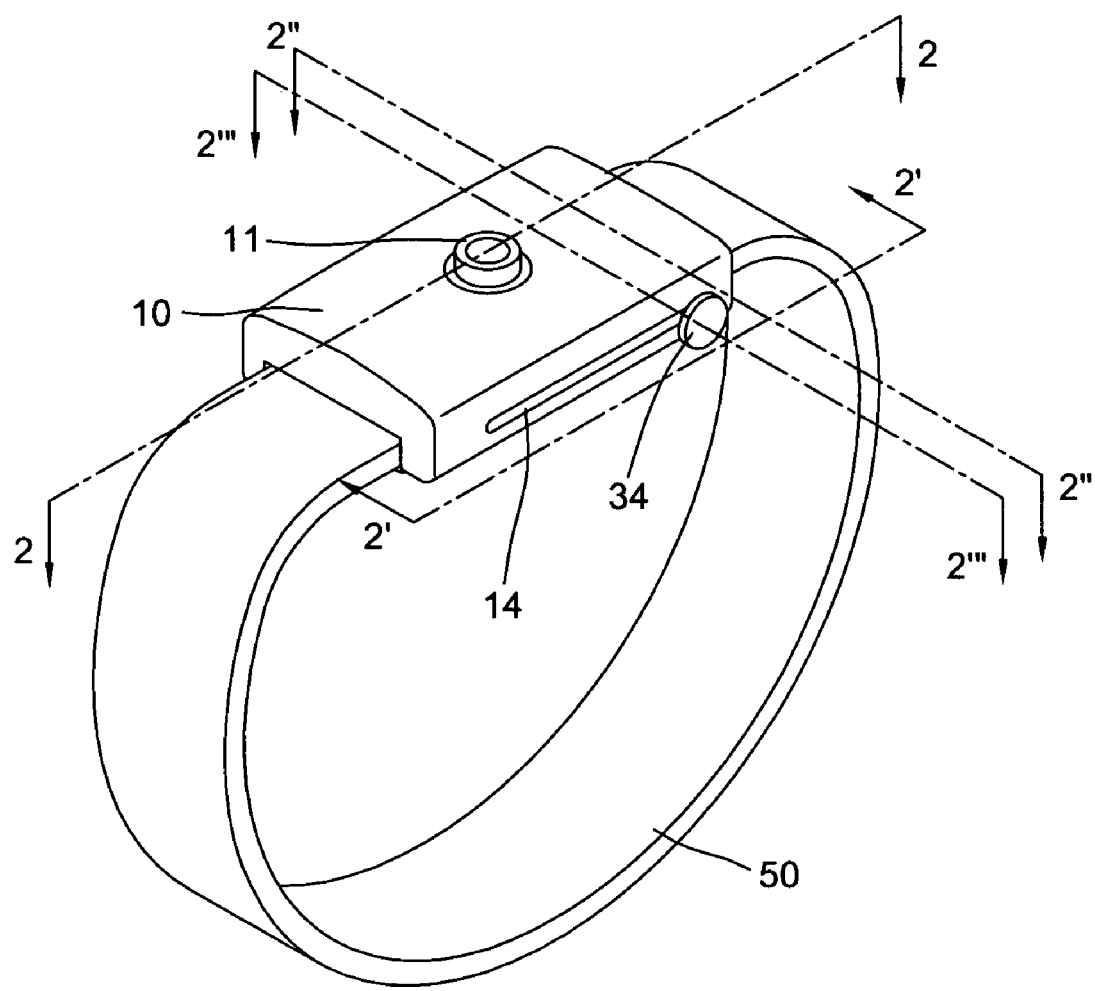
FIG. 2 is a perspective view to show the assembly of FIG. 1.
Figure 3:
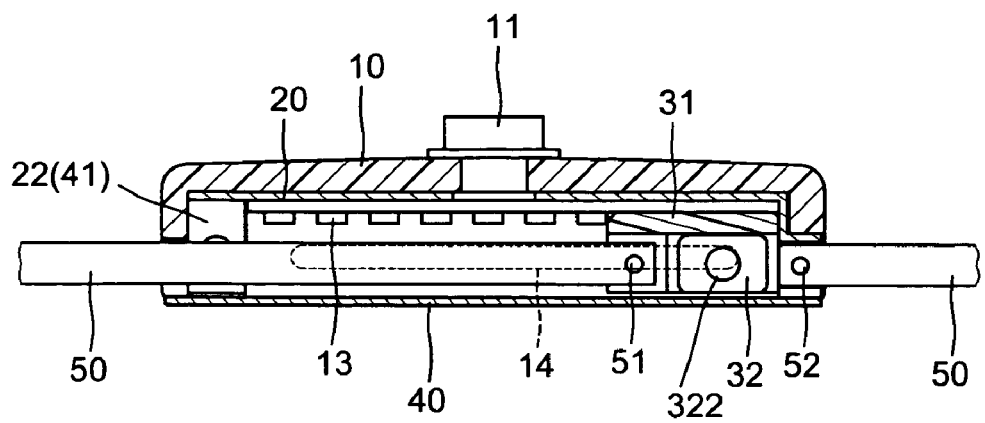
FIG. 3 is a sectional view taken along 2-2 of FIG. 2.

With reference to the drawings and initiated from FIGS. 1 to 6, the adjustable static current discharging bracelet of the present invention comprises generally a main body 10, a medium static current collector 20, a positioning device 30, a lower static current collector 40 and a link 50.

Figure 4:
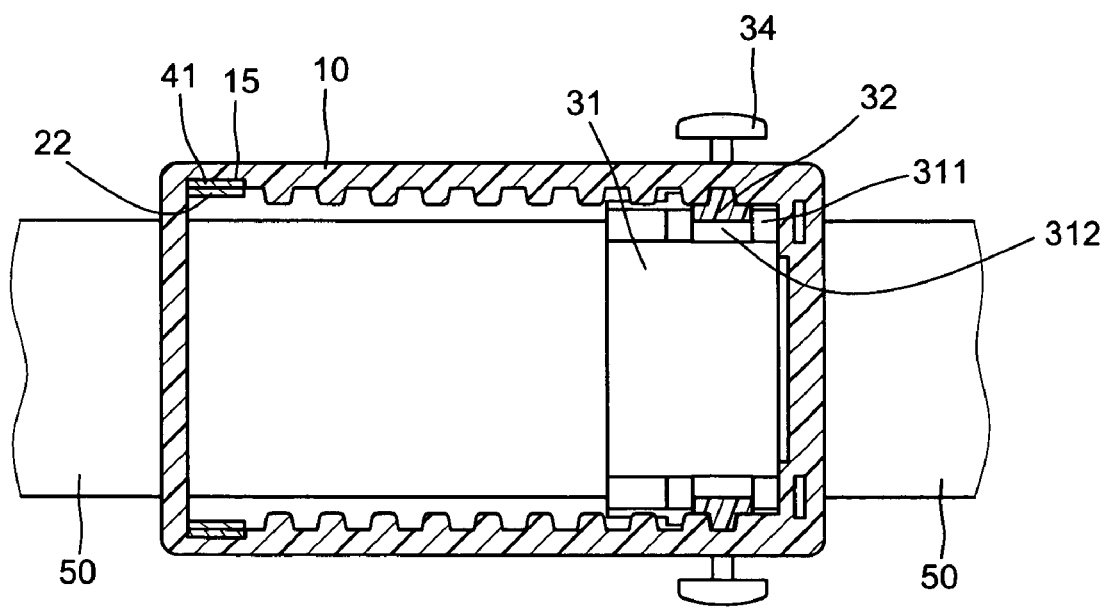
FIG. 4 is a sectional view taken along 2'-2' of FIG. 2.
Figure 5:
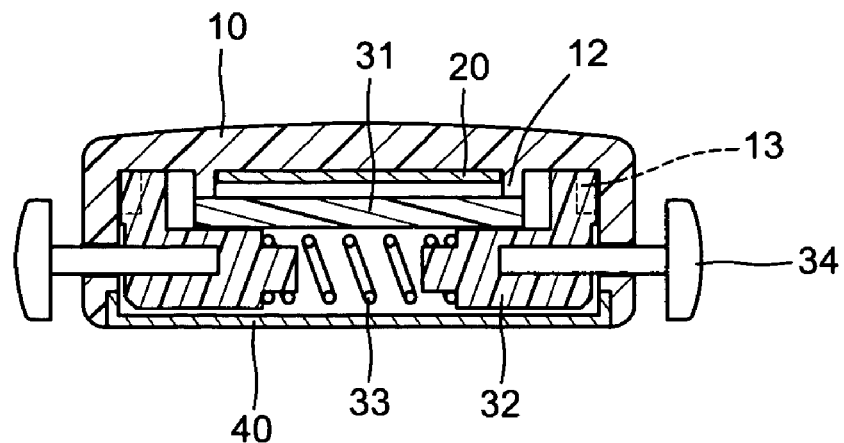
FIG. 5 is a sectional view taken along 2"-2" of FIG. 2.
Figure 6:
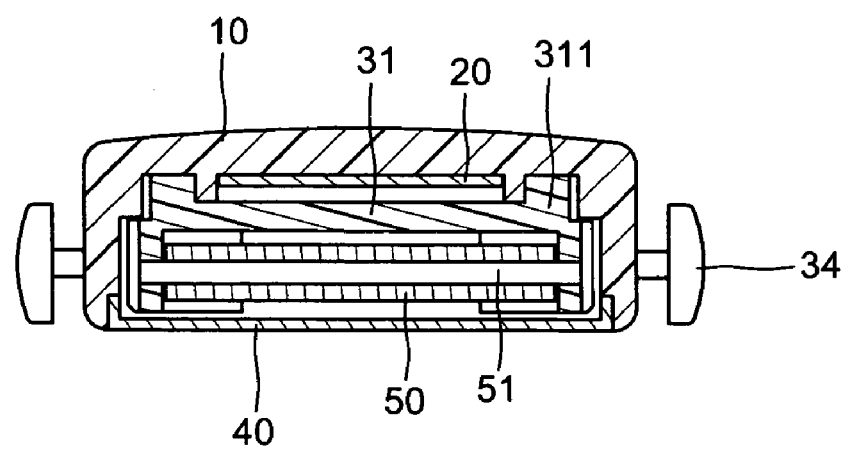
FIG. 6 is a sectional view taken along 2'''-2''' of FIG. 2.

The main body 10 has a protruding rod 11 on the central top and slightly extending to the inner side which is provided to fasten a buckle from a grounding wire (not shown), a pair of slender guides 12 parallel disposed on the opposite side of the protruding rod 11, on the inner side of the lateral walls, a pair of serrated alignment 13 are symmetrically disposed, a sliding slot 14 in the lower portion of each of the lateral walls, a inlaid groove 15 in the inner side of one end of each of the lateral walls (as shown in FIG. 4) and a pair of inlaid holes 16 symmetrically formed in the other end of the lateral walls.

The medium static current collector 20 is positioned under the inner top of the main body 10, the medium static current collector 20 is a narrow rectangular plate and has a central hole 21 riveted to the lower portion of the protruding rod 11, a large inverse U-shaped prop 22 at one end including a pair of aligned through holes 221 in its lateral portions and a smaller inverse U-shaped prop 23 at the other end including a pair of aligned through hole 231 in its lateral portions, either.

The positioning device 30 positioned under the medium static current collector 20 and has a narrow rectangular sliding plate 31, a pair of projections 311 at one side of each end of the plate 31 to define a pair of guiding gaps 312 therebetween usually sliding on the slender guide 12 of the main body 10, an aligned through hole 313 in each end abutting the projections 311, a pair of elastic retaining blocks 32 respectively engaged with the gaps 312 at two ends of the rectangular sliding plate 31 and each having a flange 321 engageable with the outer side of the gap 312, a retaining rod 322 on inner side for commonly engaging with two ends of a spring 33, a T-shaped checking plate 323 on outer end for checking the static retaining block 32 into the tooth of the serrated alignment 13 of the main body 10, an axle through hole 324 in outer end beneath the T-shaped checking plate 323 for engaging within the shank of a pair buttons 34 which are sliding within the sliding slot 14 and moving in concert with the rectangular sliding plate 31 and elastic retaining blocks 32.

The lower static current collector 40 positioned under the positioning device 30 and has a pair of upright plates 41 each including a dome 411 on outer side engaged with the aligned through holes 221 of the medium static current collector 20 and the inlaid groove 15 of the main body 10, a pair of upright plates 42 each at other end including a through hole 421 engaged with aligned through hole 231 of the medium static current collector 20 and the inlaid hole 16 of the main body 10.

The link 50 has a pair of elastic rods 52 at two lateral side of one end fixedly engaged with the through holes 421 of the lower static current collector 40, the aligned through hole 231 of the medium static current collector 20 and the inlaid hole 16 of the main body 10, a pair of elastic rods 51 at two lateral side of the other end engaged with the aligned through holes 313 of the rectangular sliding plate 31. Such that this end of the link 50 is moved in concert with the positioning device 30 to adjust its length.

Figure 7:
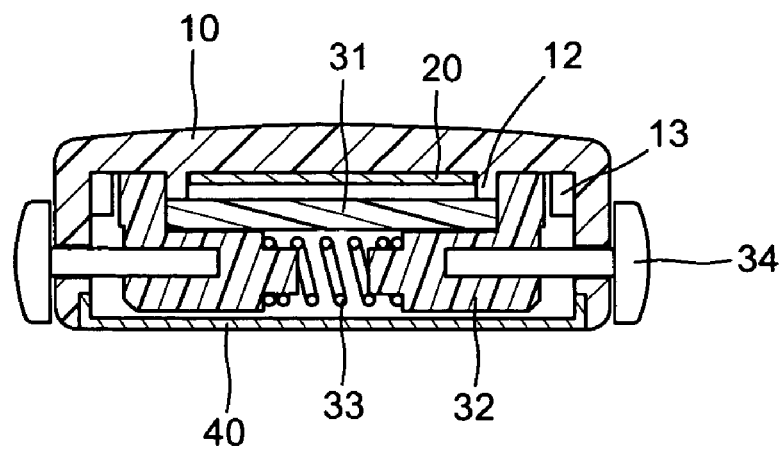
FIG. 7 is a cross sectional view to show the operation of present invention.
Figure 8:
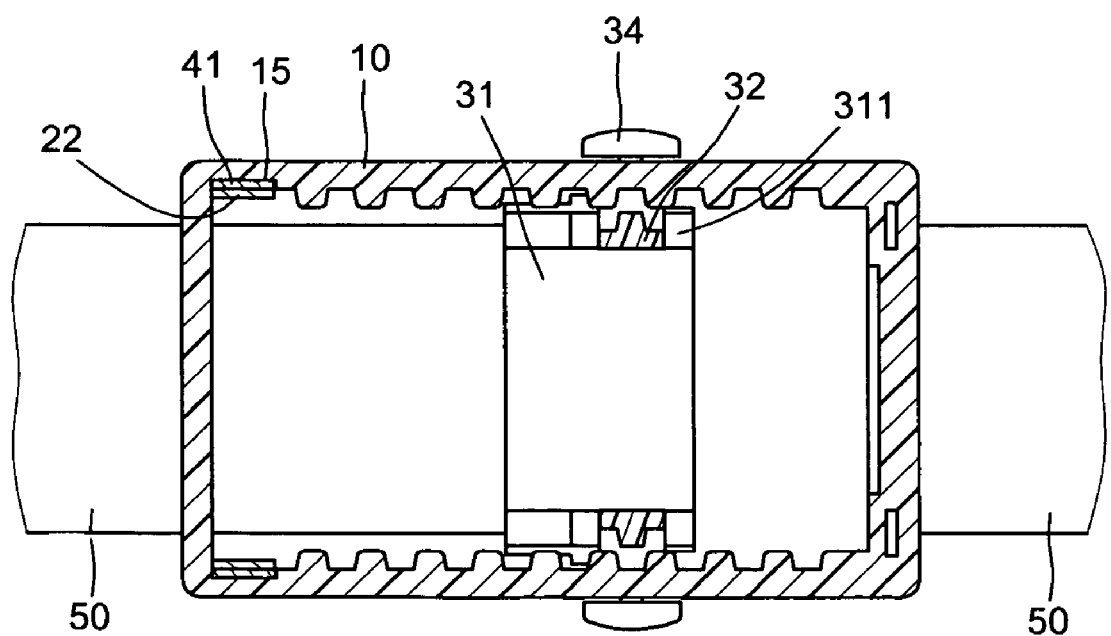
FIG. 8 is a horizontal sectional view to show the operation of present invention.
Figure 9:
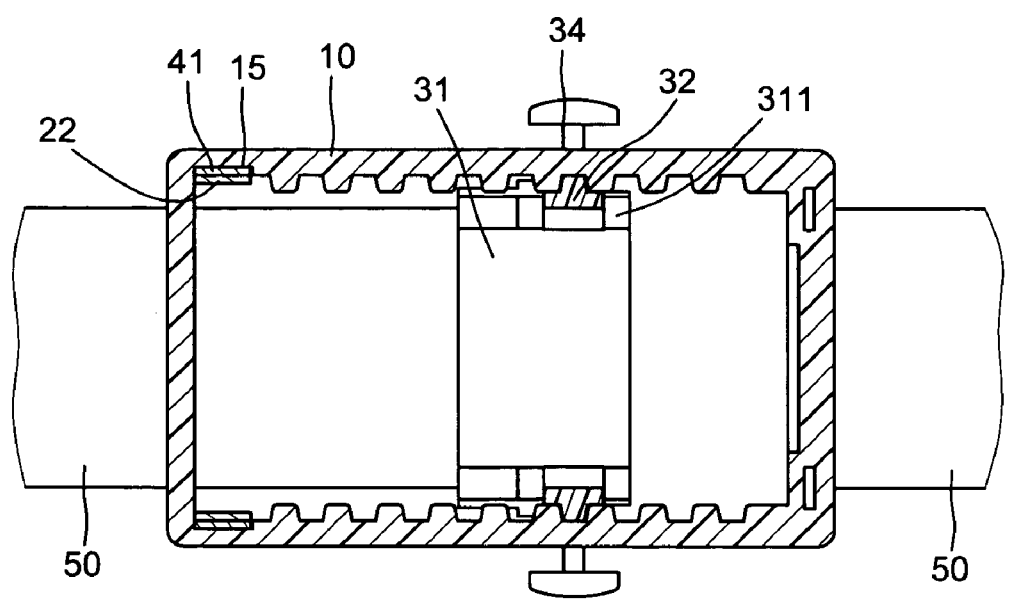
FIG. 9 is a sectional view to show that the elastic retaining block is positioned into the serrated alignment again after the length of the link is adjusted.

Referring to FIGS. 7, 8 and 9, in operation the user wears the bracelet to one wrist and uses the thumb and the index finger of other hand to press the pair of buttons 34 inward, such that the T-shaped checking plates 323 of the elastic retaining block 32 is forced to disengage with the tooth of the serrated alignment 13 so the whole positioning device is setting free together with one end of the link 50 to slide about the slender guides 12 and the sliding slot 14 to adjust the length of the link 50. When the tension of the link is suitable to the wrist, release the buttons 34 that the T-shaped checking plates 323 are engaged with the tooth of the serrated alignments 13, again, because of the resilient force of the spring 33, such that both ends of the link 50 is fixed.

The adjustment of the adjustable static current discharging bracelet of the present invention is operated by a thumb and an index finger only without opening anything. It is simple and convenient and will not be breaking-off but rapid and exact.

Note that the specification relating to the above embodiment should be construed as an exemplary rather than as a limitative of the present invention, with many variations and modifications being readily attainable by a person of average skill in the art without departing from the spirit or scope thereof as defined by the appended claims and their legal equivalents.

I claim:

1. An adjustable static current discharging bracelet comprising:
   a main body of inverse U-shaped section having a protruding rod on a central top thereof and slightly extending to inner side, a pair of slender guides parallel disposed on an inner side opposite to said protruding rod, a pair of serrated alignments symmetrically formed on upper inner side of a pair of lateral walls thereof, a pair of sliding slots symmetrically formed in a lower portion of said lateral walls, a pair of inlaid grooves symmetrically formed in an inner side of one end of said lateral walls and a pair of inlaid holes symmetrically formed in other side of said lateral walls;
   a medium static current collector positioned under inner top of said main body which is a narrow rectangular plate including a central hole riveted to a lower portion of said protruding rod, a large inverse U-shaped prop at one end of said narrow rectangular plate including a pair of first aligned through holes symmetrically formed in a pair lateral portions of said large inverse U-shaped prop and a smaller inverse U-shaped prop at other end including a pair of second aligned through holes symmetrically formed in a pair of lateral portion of said smaller inverse U-shaped prop;
   a positioning device positioned under said medium static current collector and having a narrow rectangular plate, a pair of projections at one side of each end of said plate to define a pair of guiding gaps therebetween which is provided to sliding on said slender guide of said main body, a third aligned through hole in each end thereof abutting said projections, a pair of elastic retaining blocks respectively engaged with said gaps of said sliding plate and each having a flange engageable with outer side of said gaps respectively, a retaining rod at an inner side for commonly engaging with two ends of a spring, a T-shaped checking plate projected upward on outer end for checking said elastic retaining block into tooth of said serrated alignment, an axle through hole in outer end for inserting a shank of a pair of buttons through said sliding slots respectively;
   a lower static current collector positioned under said positioning device and having a pair of first upright plate each including a dome on outer side engaged with said first aligned through holes of said medium static current collector and said inlaid grooves of said main body respectively, a pair of second upright plate each including a through hole engaged with said second aligned through hole of said medium static current collector and said inlaid holes of said main body respectively;
   a link having a pair of first and second ends, a pair of elastic rods at two lateral side of said second end fixedly engaged with said second through holes of said lower static current collector, said second aligned through holes of said medium static current collector and said inlaid holes of said main body respectively, a pair of elastic rods at two lateral side of said first end thereof engaged with said third aligned through holes of said positioning device;
   whereby, press said buttons inward to enable said elastic retaining block disengaged with said serrated alignment that said positioning device together with the first end of said link are able to slide on said slender guides to adjust the length of said link.

* * * * *